United States Patent
Beier et al.

(10) Patent No.: US 7,033,793 B2
(45) Date of Patent: Apr. 25, 2006

(54) P53 BINDING PROTEIN-RELATED PROTEIN IN CARDIOMYOPATHY

(75) Inventors: David R. Beier, Brookline, MA (US); Bruce Herron, Nassau, NY (US); Cherie Rao, Oceanside, CA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 611 days.

(21) Appl. No.: 10/171,384

(22) Filed: Jun. 14, 2002

(65) Prior Publication Data

US 2003/0031680 A1 Feb. 13, 2003

Related U.S. Application Data

(60) Provisional application No. 60/299,160, filed on Jun. 20, 2001.

(51) Int. Cl.
*C12P 21/06* (2006.01)
*C12N 1/20* (2006.01)
*C12N 15/63* (2006.01)
*C07H 21/02* (2006.01)

(52) U.S. Cl. .................. 435/69.1; 435/455; 435/252.3; 435/320.1; 536/23.1

(58) Field of Classification Search ............... 435/69.1, 435/455, 252.3, 320.1; 536/23.1
See application file for complete search history.

(56) References Cited

FOREIGN PATENT DOCUMENTS

WO    WO 00/32628    6/2000

OTHER PUBLICATIONS

White, et al., "Prion Protein-Deficient Neurons Reveal Lower Glutathione Reductase Activity and Increased Susceptibility to Hydrogen Peroxide Toxicity," *Am. J. Pathol.* 155:1723-1730 (1999).
Abstract of AF1 above.
University of Chicago Hospitals Jun. 1998 News Release, "Gene Altered Mice Boost Studies of Cardiomyopathy," www.uchospitals.edu/news/1998/19980601-ide-mouse.html.
Bradley, et al., "Embryo-Derived Stem Cells: A Tool for Elucidating the Development Genetics of the Mouse," *Current Topics in Dev. Biol.* 20:357-371 (1986).
Capecchi, "The New Mouse Genetics: Altering the Genome by Gene Targeting," *Trends in Genetics* 5:70-77 (1989).
Doetschman, et al., "Targetted Correction of a Mutant HPRT Gene in Mouse Embryonic Stem Cells," *Nature* 330:576-578 (1987).
Mansour, et al., "Disruption of the Proto-Oncogene int-2 in Mouse Embryo-Derived Stem Cells: A General Strategy for T argeting Mutations to Non-Selectable Genes," *Nature* 336:348-352 (1988).
Thomas, et al., "Site-Directed Mutagenesis by Gene Targeting in Mouse Embryo-Derived Stem Cells," *Cell* 51:503-512 (1987).
Yang, et al., "Indentification of a Novel Inhibitor of Nuclear Factor-kB, RelA-Associated Inhibitor," *J. Biol. Chem.* 274: 15662-15670 (1999).

*Primary Examiner*—Christina Chan
*Assistant Examiner*—Michail Belyavskyi
(74) *Attorney, Agent, or Firm*—Michael A. Sanzo; Fitch, Even, Tabin & Flannery

(57) ABSTRACT

The present invention is directed to a mouse model of dilated cardiomyopathy in which animals are deficient in the expression of a gene encoding a p53 binding protein-related protein (PRP). The invention also encompasses the mouse PRP gene and protein themselves as well as counterparts found in the human. The various genes and proteins can be used in making transgenic animals and in assays designed to determine the likelihood of an individual developing cardiomyopathy.

5 Claims, No Drawings

P53 BINDING PROTEIN-RELATED PROTEIN IN CARDIOMYOPATHY

CROSS REFERENCE TO RELATED APPLICATION

The present application claims the benefit of U.S. provisional application No. 60/299,160, filed on Jun. 20, 2001.

STATEMENT OF GOVERNMENT FUNDING

The United States Government has a paid-up license in this invention and the right in limited circumstances to require the patent owner to license others in reasonable terms as provided for by the terms of NIH Grant No. AR47048 awarded by the Department of Health and Human Services.

FIELD OF THE INVENTION

The present invention is directed to a mouse model of dilated cardiomyopathy. It also includes genes and proteins whose underexpression contributes to disease development and a variety of compositions and methods in which these genes and proteins are used.

BACKGROUND OF THE INVENTION

Congestive heart failure affects over 4 million people in the United States and is the most common cause of hospitalization for patients over the age of 65. A leading cause of congestive heart failure is dilated cardiomyopathy. This condition is characterized by the progressive expansion of the heart muscle and an accompanying inability to maintain adequate blood flow. Patients typically complain of fatigue, shortness of breath and chest pain. There is presently no cure for this condition and up to 50% of patients die or require a heart transplant within 5 years of diagnosis.

A model of dilated cardiomyopathy has been generated in mice by mutating CREB, a gene involved in regulating the growth and development of cardiac muscle (www.UC hospitals.edu/news/IDC.mouse.html). This model should provide a means for scientists to study disease progression and to test various therapeutic approaches. The present invention is based upon the discovery that mutations in a different gene are also involved in the development of dilated cardiomyopathy and that mice that underexpress this gene provide a distinct model of the disease. Previous studies have described a similar gene, the relA-associated inhibitor (RAI), gene in yeast and humans (Yang, et al., *J. Biol. Chem.* 274:15662–15670 (1999); WO 0032628). Because the newly identified gene encodes a protein that is homologous to p53 binding protein 2, it has been designated as the "p53 binding protein-related protein" (PRP) gene.

SUMMARY OF THE INVENTION

The present invention is based upon the discovery that mice with a spontaneous mutation in their PRP gene develop dilated cardiomyopathy. It encompasses the mouse PRP gene and protein, as well as transgenic animals that underexpress wild type protein and which, as a result, develop cardiomyopathy. In addition, the invention includes an PRP gene from humans that is distinct from similar genes that have been previously reported. By measuring the level at which this gene is expressed, an assay can be developed for assessing the likelihood of a person developing dilated cardiomyopathy.

A. Mouse PRP Gene and Protein

In its first aspect, the invention is directed to a substantially purified mouse PRP protein which has the amino acid sequence of SEQ ID NO:1. As used herein, the term "substantially purified" refers to a protein or polynucleotide that has been separated from other accompanying biological components and which typically comprises at least 85% of a sample, with greater percentages being preferred. Many means are available for assessing the purity of a protein or nucleic acid within a sample, including analysis by polyacrylamide gel electrophoresis, chromatography and analytical centrifugation.

The invention is also directed to a process for producing an antibody that binds preferentially to the mouse PRP protein described above. "Preferential binding" refers to antibodies that have at least a 100-fold greater affinity for PRP than for any other protein normally found in the mouse. Preferably, such antibodies also have a 100-fold greater affinity for mouse PRP than for similar proteins derived from other species. The invention encompasses a process for producing antibodies by administering purified mouse PRP as defined by SEQ ID NO:1 to an animal capable of antibody production. The protein should be administered at a dosage sufficient to induce antibody formation in the animal.

In another aspect, the invention is directed to a substantially pure polynucleotide encoding the mouse PRP as discussed above, to expression vectors in which such polynucleotides are operably linked to a promoter, and to host cells transformed with such vectors. The term "operably linked" refers to genetic elements that are joined in a manner that enables them to carry out their normal functions. For example, a gene is operably linked to a promoter when its transcription is under the control of the promoter and the transcript produced is correctly translated into the protein normally encoded by the gene. The term "host cell" encompasses essentially any type of cell capable of expressing the PRP gene. In a preferred embodiment, the polynucleotide has the sequence of SEQ ID NO:2.

B. DNA Construct for Homologous Recombination

The invention also includes a DNA construct suitable for homologous recombination and that can be used in the development of transgenic animals deficient in the production of normal, i.e., wild type, PRP. The construct must contain a targeting segment which has the nucleotide sequence of the endogenous PRP gene, a portion of which is interrupted or replaced with a marker sequence not normally present. Upon introduction into a host cell, the targeting segment must be capable of integrating into the genome at the site of the endogenous gene. When this occurs, a mutant PRP allele is produced that is incapable of synthesizing fully functional protein.

There are several features of the DNA construct described above which deserve further comment. First, the essential feature of the targeting segment is the ability to undergo homologous recombination at the PRP gene locus. The marker sequence which is used to interrupt or replace a portion of the targeting segment must result in a recombinant PRP sequence that has been sufficiently disrupted to result in a protein that is no longer fully functional. For example, the marker may disrupt the normal reading frame of the gene. Preferably, the marker sequence can be used in helping to select cells that have undergone homologous recombination. For example, the neomycin resistance gene may be used as a marker.

The marker nucleotide sequence is said to "interrupt" the PRP gene in instances where all of the original PRP nucleotides are still present but are separated by the marker sequence. Replacement occurs in situations where a portion of the original PRP sequence is deleted and the marker sequence takes its place. In addition to marker sequences, DNA constructs may also contain a "selection sequence" that can be used to distinguish between cells in which recombination has occurred at the PRP locus and cells where recombination has occurred at other sites in the genome. The most preferred selection sequence comprises the HSV-thymidine kinase gene. The absence of a "fully functional" PRP gene will be evidenced by the development of dilated cardiomyopathy in mice in which the deficiency is present.

Finally, it should be noted that DNA constructs may be made in which the targeting segment contains only a portion of the PRP gene provided that the portion is still capable of integrating at the site of the endogenous PRP gene. Similarly, it is not absolutely necessary that the sequence of the targeting segment be exactly complementary to the endogenous gene sequence provided that sufficient complementarity is maintained to direct the construct to the proper genomic location.

C. Transgenic Animals

The present invention encompasses a method of producing a transgenic mouse having a phenotype characterized by progressive dilated cardiomyopathy. The first step in the method involves making a DNA construct according to the procedures set forth above. The construct is introduced into mouse embryonic stem (ES) cells for the purpose of integrating the targeting fragment into the mouse genome at the PRP gene locus. Recombinant stem cells so produced are selected and then incorporated into mouse blastocysts to form chimeric embryos. These are implanted into pseudopregnant mice and allowed to develop into viable offspring. The offspring are then screened to identify heterozygous mice containing a mutant PRP gene. Finally, these mice are interbred to develop homozygous transgenic mice having the desired phenotype.

In preparing the DNA construct for use as described above, it is preferred that the marker sequence be comprised of the neomycin resistance gene and that the construct further contain the HSV-thymidine kinase gene.

In addition to the method above, the invention encompasses mice having a phenotype characterized by the development of progressive dilated cardiomyopathy and in which the mice express significantly less wild type PRP than a normal mouse of the same species. The deficiency in PRP production may be either due to less protein being made or to the production of protein that is functionally defective.

D. Human PRP Gene and Protein

In another aspect, the invention is directed to a substantially purified human PRP protein that is structurally distinct from similar proteins described in the art and which has the amino acid sequence of SEQ ID NO:3. Also included are substantially purified polynucleotides encoding the protein and expression vectors in which the polynucleotides are operably linked to a promoter. A preferred polynucleotide sequence is that of SEQ ID NO:4. Recombinant human PRP may be obtained by transforming an appropriate host cell with the expression vector.

Antibodies to purified human PRP can be developed and used in assays for quantitating the amount of PRP being produced. In this respect, the invention includes a method of determining the likelihood of a human subject developing dilated cardiomyopathy by obtaining a "test" sample of cells from the patient, determining the amount of PRP protein or mRNA present in the cells and comparing this amount with that determined for a similar "control" sample obtained from individuals known to be free of disease or from the general population. If the test sample has an amount of PRP that is significantly lower than the control sample, it may be concluded that the patient being tested has a higher than normal likelihood of developing dilated cardiomyopathy. Results may be analyzed using standard statistical methods to determine whether observed differences between test and control samples are significant. In cases where mRNA levels are measured, standard blotting techniques may be used in conjunction with nucleic acid probes that hybridize specifically to the PRP transcript.

Description of Sequences
SEQ ID NO:1: The mouse PRP protein sequence.
SEQ ID NO:2: The full length DNA coding sequence for mouse PRP.
SEQ ID NO:3: The human PRP protein sequence.
SEQ ID NO:4: DNA corresponding to the full length MRNA of human PRP.

DETAILED DESCRIPTION OF THE INVENTION

Deficiencies in cellular PRP levels, either due to low production or to the making of a protein that lacks full activity, leads to the development of progressive dilated cardiomyopathy. The PRP gene from the mouse may be used to produce transgenic animals that serve as a model for studying this disease and for testing therapies. In addition, PRP levels in humans may be assayed to determine the likelihood of an individual developing this condition.

A. Mouse and Human PRP Genes and Proteins

Any tissue or cellular source which expresses the human or mouse PRP gene (e.g., heart tissue or skin) may be used for purification. Many methods are available for obtaining substantially pure DNA sequences and may be adapted for the isolation of PRP (see e.g., Sambrook, et al., *Molecular Cloning: A Laboratory Manual*, 2nd Ed., Cold Spring Harbor Press (1989)). Alternatively, gene sequences may be synthesized using standard procedures or obtained in large amounts using the polymerase chain reaction (PCR). Primers suitable for performing PCR may be based upon the sequences provided herein in the Sequence Listing.

In order to express protein, the PRP gene structural sequence must be placed in a vector containing transcriptional and translational signals that are recognized by a host cell. Cloned PRP sequences should be inserted into an expression vector in an operable linkage, i.e. they should be positioned so as to be under the control of regulatory sequences found in the vector and in such a manner that mRNA is produced which is correctly translated into the PRP amino acid sequence.

Expression of a protein in different hosts may result in different post-translational modifications that can, potentially, alter the properties of the protein. Preferably, nucleic acid encoding PRP is expressed in eukaryotic cells, especially mammalian cells. These cells provide post-translational modifications which inter alia aid in the correct folding of the protein. Mammalian cells that may be used include, without limitation, NIH-3T3 cells, CHO cells, HeLa cells, LM(tk$^-$) cells, etc. Vectors suitable for each of these cell types are well known in the art (see e.g., Sambrook, et al. *supra*). Preferred eukaryotic promoters include that of the mouse metallothionein I gene, the TK promoter of herpes virus; the SV 40 early promoter, and the CMV early promoter. Examples of suitable prokaryotic promoters include those capable of recognizing T4 polymerases, the $P_R$ and $P_L$ promoters of bacteriophage lambda, and the Trp, recA, heat shock and LacZ promoters of *E. coli*. Expression vectors may be introduced into host cells by methods such as calcium phosphate precipitation, microinjection, electroporation and viral transfer. Cells expressing recombinant polypeptide can be selected using methods well known in the art. One simple method for confirming the presence of desired sequences is to perform PCR amplification as discussed above.

Recombinant protein may be purified using standard techniques such as filtration, precipitation, chromatography and electrophoresis. Purity can be assessed by performing electrophoresis in a polyacrylamide or agarose gel and visualizing proteins using standard staining techniques. The purified proteins may be used as controls in assays for determining the level of PRP produced in a cellular sample and for making antibodies that can be used in such assays. Polynucleotides can be used for recombinantly making protein and the DNA corresponding to the endogenous mouse PRP gene may be used in constructs for the production of transgenic animals.

B. Antibodies to PRP Proteins

The present invention includes antibodies that bind preferentially to PRP and to a process for producing such antibodies. The process involves injecting either the entire PRP protein into an appropriate animal or injecting short peptides from specific regions of the protein. Methods for making and detecting antibodies are well known to those of skill in the art as evidenced by standard reference works such as: Harlow, et al. *Antibodies, A Laboratory Manual*, Cold Spring Harbor Laboratory, N.Y. (1988); Klein, *Immunology: The Science of Self-Nonself Discrimination* (1982); and Campbell, "Monoclonal Antibody Technology, in: *Laboratory Techniques in Biochemistry and Molecular Biology* (1984)).

The antibodies may be used to detect PRP in any of a variety of immunoassays. For example, antibodies may be used in radioimmunoassays or immunometric assays, also known as "two-site" or "sandwich" assays (see Chard, "An Introduction to Radioimmune Assay and Related Techniques," in: *Laboratory Techniques in Biochemistry and Molecular Biology*, North Holland Publishing Co., N.Y. (1978)). In a typical immunometric assay, a quantity of unlabeled antibody is bound to a solid support that is insoluble in the fluid being tested, e.g., blood, lymph, cellular extracts, etc. After the initial binding of antigen to immobilized antibody, a quantity of detectably labeled second antibody (which may or may not be the same as the first) is added to permit detection and/or quantitation of bound antigen (see e.g., Kirkham, et al., *Radioimmune Assay Method*, (1970)). Many variations of these types of assays are known in the art and may be employed in connection with the present invention.

Antibodies to PRP may also be used in purification procedures (see generally, Dean et al., *Affinity Chromatography, A Practical Approach*, IRLP Press (1986)). Typically, antibody is immobilized on a chromatographic matrix such as Sepharose 4B™. The matrix is then packed into a column and the preparation containing PRP is passed through under conditions that promote binding, e.g, under conditions of low salt. The column is then washed and bound protein is eluted using a buffer that promotes dissociation from antibody, e.g., buffer having an altered pH or salt concentration. The eluted protein may be transferred to a buffer of choice, e.g., by dialysis, and either stored or used directly.

C. DNA Constructs for Homologous Recombination

The DNA constructs of the invention are often referred to in the literature as "knockout" constructs because of their use in disrupting normally active genes. Typically, they contain a relatively long (>1 Kb) targeting segment that has a sequence highly homologous to an endogenous gene in a host cell and that is disrupted by a non-homologous marker sequence. The targeting segment used in constructs may be derived from either genomic or cDNA molecules by standard methods (see, e.g., Sambrook, et al., supra). For example, a portion of the PRP gene may be isolated using PCR amplification based upon its known sequence. Alternatively, the targeting segment in a construct may be made using chemical synthesis methods.

In order to incorporate a marker sequence, the targeting segment can be digested with one or more restriction enzymes selected to cut at specific locations. Any location which produces a sufficient disruption of the PRP gene to result in the elimination of a functional gene product after homologous recombination will suffice. Thus, disruption may take place either within the structural sequence of PRP or at a regulatory element, e.g., the promoter of the gene.

The marker sequence used in constructs will typically be an antibiotic resistance gene or other gene whose expression can be easily detected and which is not normally present in the host. The marker gene may be expressed in the host cell either as a result of its being operably linked to a promoter in the construct, or by coming under of the control of the native PRP gene promoter as a result of homologous recombination. In cases where it is part of the construct, the promoter should be selected based upon its having a high activity in the particular host cell undergoing homologous recombination. A typical example of a promoter suitable for use in mouse cells is the promoter of the phosphoglycerate kinase gene. The most preferred gene for use as a marker is a neomycin resistance gene (Neo). Cells which have integrated Neo into their genome and which are expressing this gene are resistant to G418. Thus, a simple means is provided for selecting recombinant cells. In addition to a promoter, the marker gene will typically have a polyA sequence attached to its 3' end.

In addition to having a marker gene for disrupting the PRP sequence and for identifying cells that have undergone homologous recombination, the constructs of the present invention will typically include a gene that can be used for distinguishing between cells in which recombination has occurred at the PRP gene locus and cells in which recombination has occurred elsewhere in the genome. Preferably, this "selection sequence" will consist of the HSV-thymidine kinase gene under the control of an appropriate promoter. The combination of a marker sequence for selecting all cells that have undergone homologous recombination and a selection sequence for distinguishing site specific integration from random integration has been termed "positive-negative selection" and details of both the procedure and the production of constructs appropriate for the procedure are well known in the art (see Capecchi, M., *TIG* 5:70 (1989); Mansour et al., *Nature* 36:348 (1988); Thomas, et al., *Cell* 51:503 (1987); and Doetschman, et al., *Nature* 330:576 (1987)).

The DNA construct for disruption of the PRP gene may be transfected directly into a host cell or it may first be placed in a vector for amplification prior to transfection. Preferred vectors are those that are rapidly amplified in bacterial cells such as the pBluescript II SK vector (Stratagene, San Diego Calif.) or pGEM 7 (Promega Corp., Madison, Wis.).

D. Production of ES Cells Comprising DNA Constructs

ES cells suitable for transfection by the constructs described above can be selected based upon their ability to integrate into and become part of the germ line of a developing embryo. Any ES cell line that has this characteristic may be used, e.g., the murine cell line D3 (ATCC, 12301 Parklawn Drive, Rockville, Md., Catalog No. CRL1934). After appropriate host cells have been chosen, they are cultured and prepared for DNA insertion using methods known in the art (see, e.g., Robertson in: *Teratocarcinomas and Embryonic Stem Cells: A Practical Approach*, E. J. Robertson, Ed., IRL Press, Washington, D.C. (1987); Bradley, et al., *Curr. Topics in Devel. Biol.* 20:357–371 (1986); and Hogan, et al, *Manipulating the Mouse Embryo: A Laboratory Manual*, Cold Spring Harbor Laboratory Press, Cold Spring Harbor N.Y. (1986)).

The introduction of PRP constructs into host cells can be accomplished using any of a variety of methods such as electroporation, microinjection or calcium phosphate treatment. The preferred method of insertion is electroporation. If the DNA construct has been inserted into a vector, it is preferred that the DNA be linearized prior to transfection. Linearization can be accomplished by digesting the DNA vector with a restriction endonuclease selected to cut outside of the PRP construct sequence.

The screening of transfected cells can be carried out using several different methods. In the cases where an antibiotic resistance gene has been used as a marker, the cells can be cultured in the presence of antibiotic to identify recombinants. In cases where other types of markers are used, Southern hybridizations may be carried out using labeled probes specific for the marker sequence. Finally, if the marker gene encodes an enzyme whose activity can be detected, e.g., beta-galactosidase, enzymatic assays may be performed.

It will usually be desirable not only to identify cells in which recombination has occurred, but also to distinguish specific recombination, i.e., integration at the PRP gene locus, from random insertion events occurring elsewhere in the genome. To identify cells with proper integration, chromosomal DNA can be extracted from cells using standard methods and Southern hybridizations can be performed using probes designed to hybridize specifically to DNA derived from constructs. Alternatively, PCR amplification can be performed using primers that will only act in cells where homologous recombination has occurred at the PRP locus or which will produce a distinctive product of known size.

One way to enrich preparations for recombinants modified at the PRP locus is to incorporate the HSV-thymidine kinase gene into constructs at a position adjacent to the targeting segment. The construct is designed so that the HSV-tk gene is only transferred to the host cell genome when recombination occurs at the PRP gene site. Because the HSV-tk gene makes cells susceptible to the drug gancyclovir, the exposure of recombinants to this drug will negatively select against cells in which random integration has occurred (see Mansour, et al., *Nature* 336:348 (1988)).

It will be appreciated that homologous recombination will result in the disruption of one PRP allele much more frequently than in the disruption of both alleles. If one desires to produce cells that are completely deficient in the PRP gene, it may therefore be necessary to conduct a second round of homologous recombination on cells that have already been selected as having one allele disrupted. In the second round of transfection, a marker should be used that is different from the marker used in producing the initial recombinants. For example, if a neomycin resistance gene was used to produce cells with one disrupted allele, beta-galactosidase may be used as a marker in the second construct. Screening for cells that have incorporated DNA at the PRP site may be carried out as described above.

E. Making of Transgenic Animals that Develop Dilated Cardiomyopathy

Embryonic stem cells engineered to contain a mutant PRP allele and produced by homologous recombination as described above, may be used to make transgenic animals with a substantial absence of functional PRP protein. These animals are characterized by the progressive development of dilated cardiomyopathy.

The first step in the making of transgenic animals is to produce ES cells modified by homologous recombination to contain a mutant PRP gene allele. This may be accomplished using the procedures described above. The next step is to incorporate the mutant ES cells into an embryo. The preferred method for accomplishing this is by microinjection into an embryo at the blastocyst stage of development. In mice, blastocysts at about 3.5 days of development may be obtained by perfusing the uterus of pregnant animals (Bradley, in: *Teratocarcinomas and Embryonic Stem Cells: A Practical Approach*, Robertson, ed., IRL Press, Washington, D.C. (1987)). Preferred blastocysts are male and have genes coding for a coat color or other phenotypic marker that is different from the corresponding marker encoded by the stem cells. In this way, offspring are produced that can be easily screened for the presence of mutant PRP alleles. For example, if the ES cell line carries the gene for a white coat, the embryo selected will, preferably, carry the gene for a black or brown coat and offspring carrying a mutant PRP allele should have mosaic coats.

After the embryonic stem cells have been incorporated into the blastocyst, the chimeric embryo is implanted into the uterus of a pseudopregnant animal. Such animals may be prepared by mating females with vasectomized males of the same species. The pseudopregnant stage of the female is important for successful implantation and, for mice, females about two or three days pseudopregnant should typically be used.

After chimeric embryos have been implanted into pseudopregnant animals, they are allowed to develop to term and offspring are then screened for the presence of a mutant PRP allele. In cases where a phenotype selection strategy has been employed, e.g., based upon coat color as described above, initial screening may be accomplished by simple inspection of animals for mosaic coat color or some other readily apparent phenotypic marker. In addition, or as an alternative, chromosomal DNA may be obtained from the tissue of offspring, e.g., from the tail tissue of mice, and screened for the presence of a modified nucleotide sequence at the PRP gene locus using Southern blots and/or PCR amplification.

Once offspring have been identified carrying the PRP gene mutation, they can be interbred to produce homozygous animals characterized by an impaired synthesis of functional PRP and the development of cardiomyopathy. Heterozygotes may be identified using Southern blots or PCR amplification as described above. Homozygotes may be identified by Southern blotting equivalent amounts of genomic DNA obtained from the offspring of crossed heterozygotes, from the heterozygotes themselves, an from wild-type animals. Probes should be designed to bind to a portion of the PRP gene sequence present in all animals and the presence of mutant alleles can be determined by the relative position of the bands in autoradiographs. Alternatively, analysis may be performed based upon the relative sizes of PCR amplification products.

Other means for identifying and characterizing transgenic animals are also available. For example, Northern blots can be used to probe mRNA obtained from tissues of offspring animals for the presence or absence of transcripts encoding the PRP gene, the marker gene, or both. In addition, Western blots may be used to assess PRP expression by probing with antibodies specific for the protein. Once heterozygous transgenic animals have been identified, they may be interbred to provide a continual supply of animals that can be used in studying progressive dilated cardiomyopathy and in evaluating drugs to determine whether they have a beneficial effect in slowing the progression of the disease.

F. Assay Method Based Upon Human PRP

Based upon the concepts set forth above, it may be concluded that individuals with abnormally low levels of PRP or which produce a mutated form of PRP are at increased risk of developing dilated cardiomyopathy. Thus, assays may be performed using cellular "test" samples from an individual to provide diagnostic information. Assays for determining the amount of PRP expressed should be designed to detect either the human PRP protein shown as SEQ ID NO:3 or mRNA coding for this protein. Many methods that are standard in the art may be used for this purpose including radioimmunoassays, immunometric assays and blotting assays which utilize nucleic acid probes that hybridize to PRP transcripts. The results of such an assay performed on a test sample should be compared to those determined using samples derived from individuals known to be normal in the sense that they do not have dilated cardiomyopathy. This "control" population should typically be comprised of a large number of individuals. Standard statistical analyses may be performed to determine whether differences observed between test and control samples are significant.

To test for mutations in the PRP gene, PCR may be performed on test samples, e.g., samples from cheek brushes or the buffy coats from blood. Routine procedures for determining the sequence of a gene may then be used.

All references cited are incorporated in their entirety herein by reference. Having now fully described the invention, those skilled in the art will understand that the invention may be practiced within a wide range of conditions, parameters, and the like, without affecting the spirit or scope of the invention or any embodiment thereof.

What is claimed is:

1. A substantially pure polynucleotide, wherein said polynucleotide consists of a sequence encoding the PRP protein, wherein said protein comprises the amino acid sequence of SEQ ID NO:1.

2. A vector for recombinantly expressing mouse PRP, comprising a coding region consisting of the polynucleotide of claim 1 operably linked to a promoter.

3. An isolated host cell transformed with the vector of claim 2.

4. The polynucleotide of claim 1, wherein said polynucleotide comprises the sequence of SEQ ID NO: 2.

5. A DNA construct suitable for homologous recombination, comprising a targeting segment consisting of the nucleotide sequence of SEQ ID NO:2, wherein:

(a) a portion of the nucleotide sequence of said targeting segment has been interrupted or replaced with a marker nucleotide sequence;

(b) said targeting segment is capable of integrating into the genome of a mouse host cell at the site of the endogenous PRP gene when said construct is introduced into said mouse host cell; and (c) a mutant allele is produced which is incapable of synthesizing a fully functional PRP gene product when said targeting segment is integrated at the site of said endogenous PRP gene.

* * * * *

SEQUENCE LISTING

```
<160> NUMBER OF SEQ ID NOS: 4

<210> SEQ ID NO 1
<211> LENGTH: 824
<212> TYPE: PRT
<213> ORGANISM: mouse

<400> SEQUENCE: 1

Met Asp Ser Glu Ala Phe Gln His Ala Arg Asp Leu Leu Asp Leu Asn
1               5                   10                  15

Phe Gln Ser Leu Ala Met Lys His Met Asp Leu Lys Gln Met Glu Leu
                20                  25                  30

Asp Thr Ala Ala Ala Lys Val Asp Glu Leu Thr Lys Gln Leu Glu Ser
            35                  40                  45

Leu Trp Ser Asp Ser Pro Ala Pro Pro Gly Ala Gln Ala Gly Val Pro
    50                  55                  60

Ser Arg Met Ala Arg Tyr Ser Thr Ser Pro Val Pro Glu His Phe Gly
65                  70                  75                  80

Ser Arg Gly Ser Pro Gln Lys Ile Ala Thr Asp Gly Ile Glu Ala Arg
                85                  90                  95

Phe Gly Arg Ser Glu Ser Ala Pro Ser Leu His Pro Tyr Ser Pro Leu
            100                 105                 110

Ser Pro Lys Gly Arg Pro Ser Pro Arg Thr Pro Ile Tyr Leu Gln
            115                 120                 125

Pro Asp Thr Tyr Ser Ser Leu Asp Arg Ala Pro Ser Pro Arg Pro Arg
    130                 135                 140

Ala Phe Asp Gly Ala Gly Ser Pro His Gly Arg Ala Pro Ser Pro Arg
145                 150                 155                 160

Pro Gly Ile Gly Pro Val Arg Gln Pro Gly Pro Ser Thr Pro Phe Asp
                165                 170                 175

Tyr Leu Gly Arg Ala Gly Ser Pro Arg Gly Ser Pro Leu Ala Glu Gly
            180                 185                 190

Pro Gln Ala Phe Phe Pro Glu Arg Gly Pro Ser Pro Arg Pro Pro Ala
        195                 200                 205
```

-continued

```
Ala Ala Tyr Asp Thr Ala Gly Thr Phe Gly Ser Pro Leu Leu Gly Ala
    210                 215                 220
Gly Gly Ser Ala Phe Thr Pro Pro Leu Arg Ala Gln Asp Asp Ser Thr
225                 230                 235                 240
Leu Arg Arg Arg Pro Pro Lys Ala Trp Asn Glu Ser Asp Leu Asp Val
                245                 250                 255
Ala Tyr Glu Lys Lys Ser Ser Gln Thr Ala Ser Tyr Glu Arg Leu Asp
            260                 265                 270
Val Phe Thr Arg Pro Ala Ser Pro Gly Leu Gln Leu Leu Pro Trp Arg
        275                 280                 285
Glu Ser Ser Leu Asp Gly Leu Gly Ala Ser Gly Lys Asp His Leu Thr
    290                 295                 300
Ser Ala Thr Leu Pro Arg Asn Tyr Lys Val Ser Pro Leu Ala Ser Asp
305                 310                 315                 320
Arg Arg Ser Asp Val Gly Ser Tyr Arg Arg Ser Leu Gly Ser Ala Gly
                325                 330                 335
Pro Ser Gly Thr Leu Pro Arg Ser Trp Gln Pro Val Ser Arg Ile Pro
            340                 345                 350
Met Pro Pro Ser Ser Pro Gln Pro Arg Ser Thr Pro Arg Gln Arg Pro
        355                 360                 365
Ile Pro Leu Ser Met Ile Phe Lys Leu Gln Asn Ala Phe Trp Glu His
    370                 375                 380
Gly Ala Gly Arg Ala Val Leu Pro Gly Ser Pro Ile Phe Ser Arg Ala
385                 390                 395                 400
Pro Pro Pro Lys Leu Pro Pro Gln Pro Pro Gln Pro Gln Met Gln
                405                 410                 415
Pro Gln Pro Gln Pro Gln Pro Gln Met Gln Pro Gln Ser Gln Ala Gln
            420                 425                 430
Pro Gln Thr Pro Ala Pro Gln Gln Thr Trp Ser Pro Met Asn Glu Gly
        435                 440                 445
Leu Leu Lys Ser Pro Ala Glu Leu Glu Pro Glu Pro Glu Leu Glu Val
    450                 455                 460
Leu Leu Ala Pro Val Glu Glu Ala Gly Asp Ala Asp Glu Gly Thr Val
465                 470                 475                 480
Thr Arg Pro Leu Ser Pro Thr Arg Leu Gln Pro Ala Leu Pro Pro Glu
                485                 490                 495
Ala Gln Thr Val Pro Glu Leu Glu Glu Val Ala Arg Val Leu Ala Glu
            500                 505                 510
Ile Pro Arg Pro Leu Lys Arg Arg Gly Ser Met Glu Gln Ser Pro Ala
        515                 520                 525
Val Ala Leu Pro Pro Thr His Lys Lys Gln Tyr Gln Gln Ile Ile Asn
    530                 535                 540
Arg Leu Phe His Arg His Gly Pro Gly Pro Gly Pro Glu Pro
545                 550                 555                 560
Glu Leu Ser Thr Ile Thr Glu Gly Ser Glu Ala Arg Ala Gly Pro Pro
                565                 570                 575
Ala Pro Ala Pro Pro Ala Pro Ile Pro Pro Ala Pro Pro Gln Ser
            580                 585                 590
Ser Pro Pro Glu Gln Pro Gln Ser Met Glu Met Arg Ser Val Leu Arg
        595                 600                 605
Lys Val Gly Ser Pro Arg Lys Ala Arg Arg Ala Arg Leu Asn Pro Leu
    610                 615                 620
```

| Val | Leu | Leu | Leu | Asp | Ala | Ala | Leu | Thr | Gly | Glu | Leu | Asp | Val | Val | Gln |
| 625 | | | | 630 | | | | 635 | | | | 640 | | | |

| Gln | Ala | Val | Lys | Glu | Met | Asn | Asp | Pro | Ser | Gln | Pro | Asn | Glu | Glu | Gly |
| | | | | 645 | | | | 650 | | | | 655 | | | |

| Ile | Thr | Ala | Leu | His | Asn | Ala | Ile | Cys | Gly | Ala | Asn | Tyr | Pro | Ile | Val |
| | | 660 | | | | 665 | | | | 670 | | | | | |

| Asp | Phe | Leu | Ile | Ala | Ala | Gly | Ala | Asn | Val | Asn | Ser | Pro | Asp | Ser | His |
| | | 675 | | | | 680 | | | | 685 | | | | | |

| Gly | Trp | Thr | Pro | Leu | His | Cys | Ala | Ala | Ser | Cys | Asn | Asp | Thr | Ala | Ile |
| 690 | | | | 695 | | | | 700 | | | | | | | |

| Cys | Thr | Ala | Leu | Val | Gln | His | Gly | Ala | Ala | Ile | Phe | Ala | Thr | Thr | Leu |
| 705 | | | | 710 | | | | 715 | | | | | | 720 | |

| Ser | Asp | Gly | Ala | Thr | Ala | Ile | Glu | Lys | Cys | Asp | Pro | Tyr | Arg | Glu | Gly |
| | | | | 725 | | | | 730 | | | | 735 | | | |

| Tyr | Ala | Asp | Cys | Ala | Thr | Tyr | Leu | Ala | Asp | Val | Glu | Gln | Ser | Met | Gly |
| | | | 740 | | | | 745 | | | | 750 | | | | |

| Leu | Met | His | Asn | Gly | Val | Val | Tyr | Ala | Leu | Trp | Asp | Tyr | Ser | Ala | Glu |
| | | 755 | | | | 760 | | | | 765 | | | | | |

| Phe | Gly | Asp | Glu | Leu | Ser | Phe | Arg | Glu | Gly | Ser | Val | Thr | Val | Leu | |
| 770 | | | | | 775 | | | | | 780 | | | | | |

| Arg | Arg | Asp | Gly | Pro | Glu | Glu | Thr | Asp | Trp | Trp | Trp | Ala | Ser | Leu | His |
| 785 | | | | 790 | | | | 795 | | | | | | 800 | |

| Gly | Gln | Glu | Gly | Tyr | Val | Pro | Arg | Asn | Tyr | Phe | Gly | Leu | Phe | Pro | Arg |
| | | | | 805 | | | | 810 | | | | 815 | | | |

| Val | Lys | Ser | Gln | Arg | Ser | Lys | Ile |
| | | | 820 | | | | |

```
<210> SEQ ID NO 2
<211> LENGTH: 2575
<212> TYPE: DNA
<213> ORGANISM: mouse

<400> SEQUENCE: 2
cgctccccgc cgctggagcc ggagccggag cccgaggaaa agccccccgg tgccaggatc        60
tgccccgacg cacaggcacc ctgctccggc cggcaccatg gacagcgaag cattccagca       120
tgcgagggac cttctggacc tgaacttcca gtcactggcc atgaagcaca tggatctgaa       180
acagatggag ctggacaccg ctgccgccaa agtggacgaa ttaaccaagc agttagagtc       240
gttgtggtca gactcgccag ctcctcctgg cgctcaggct ggagtcccct ctaggatggc       300
ccggtacagc accagcccgg tccccgagca ttttggcagc agagggtcac ctcagaagat       360
agccaccgat ggcatagagg cccgtttttgg acgctcggag agtgccccgt ccctgcaccc      420
ttacagccct ctgtctccca agggccgtcc gtcttcaccg cgcaccccta tctacctgca       480
gcctgacacc tacagcagcc tagatcgggc gccatcgccc agaccccgcg ccttcgatgg       540
agcgggcagc ccccatggtc gggcaccgtc cccgaggccg gggattggcc cggtgcggca       600
gcctggtccc tcgaccccct ttgactatct gggccgcgca gggtccccct ggggcagccc       660
tctagctgag gggccccagg ccttcttccc ggagcgagga cctcccccac gtccgcctgc       720
tgcagcctac gacacagcgg gcacgttcgg gagccctctg ctgggcgcgg gtggcagtgc       780
cttcaccccg ccgcttcgtg cacaagatga ctcgacgctg gccggaggc ccccgaaggc       840 ctggaacgag tctgacttgg atgtagccta cgagaaaaag tcttcacaga cagcaagcta       900
cgaacggctg gatgtcttca cacggcctgc ctctccgggc ctgcagctct accctggag       960
```

-continued

```
agagagcagc ctggatgggc tgggggccag yggcaaggac cacctcacca gcgccactct    1020
gccacgcaat tacaaggtgt ctcctctggc cagtgacagg cgttctgacg ttggcagcta    1080
ccgccgctct ttgggctctg cagggccctc aggcactttg cccgcagct ggcagcccgt     1140 cagccgcatc cccatgcccc cctctagccc acagccccgc agcaccccac gccagcgccc    1200 catcccctc agtatgatct ttaaaactcca gaatgctttc tgggaacatg gagccggcag    1260
ggctgtgctc ccgggatccc ccatcttctc ccgagcaccc ccacctaagc tgcctcccca    1320 gccacccct cagccacaga tgcaacccca accccaaccc caacctcaga tgcagcccca     1380
gtcccaggcc cagcctcaga ctccagcacc tcaacagact tggtctccca tgaatgaagg    1440
cctcctcaaa tcccctgccg agctggagcc cgagcccgag ctggaggtgc tactggctcc    1500
tgtggaggag gccggggatg cagatgaagg cacggtcacg cggcccctca gcctaccag     1560 gctgcagcca gcgctgccac cggaagcaca gactgtaccc gagctggagg aggtggcccg    1620
agtgctggca gagattcctc gaccctcaa acgcagaggc tccatggagc agagccctgc     1680
agtggcgctg cctcccaccc acaagaaaca ataccaacag atcatcaata gactcttcca    1740
tcggcacggc ggcccagggc ctggagggcc tgagccggag ctgtccacaa ttacagaggg    1800
atctgaagcc agggcagggc ccctgctcc cgccccacca gctcctatcc caccccagc     1860 cccaccccag agcagccctc cagagcagcc tcagagcatg gagatgcgct cagtactgcg    1920
caaagtgggg tccccgcgca aggcccggcg tgctcgcctc aatccactgg tgctgctgtt    1980
ggatgcagcg ctgactggag agttggacgt ggtacagcag gcggtgaagg agatgaacga    2040
cccaagccag cccaacgagg agggcatcac cgccctgcac aatgccatct gcggtgccaa    2100
ctaccccatc gtggacttcc tcatcgctgc gggcgccaac gtcaactccc ctgacagcca    2160
cggctggacg ccactgcatt gtgccgcttc ctgcaatgac actgccatct gcacagcatt    2220
ggtgcaacat ggtgcggcca tcttcgccac cactctcagt gacggcgcca ccgccatcga    2280
aaagtgcgac ccttaccgcg agggctatgc agactgtgcc acctacctgg cagacgtgga    2340
acaaagcatg ggactgatgc acaatggcgt tgtgtatgca ctctgggact acagcgcaga    2400
gtttggggat gagctgtctt tccgagaggg cgagtcagtc actgtgctgc ggagagatgg    2460
gccagaggag actgattggt ggtgggcctc actgcacggc caggaaggct atgtgccgcg    2520
caactacttc gggctcttcc ctagagtgaa gtctcagcgg agcaaaatct agtag          2575
```

<210> SEQ ID NO 3
<211> LENGTH: 827
<212> TYPE: PRT
<213> ORGANISM: Homo sapiens

<400> SEQUENCE: 3

```
Met Asp Ser Glu Ala Phe Gln Ser Ala Arg Asp Phe Leu Asp Met Asn
1               5                   10                  15

Phe Gln Ser Leu Ala Met Lys His Met Asp Leu Lys Gln Met Glu Leu
                20                  25                  30

Asp Thr Ala Ala Lys Val Asp Glu Leu Thr Lys Gln Leu Glu Ser
            35                  40                  45

Leu Trp Ser Asp Ser Pro Ala Pro Gly Pro Gln Ala Gly Pro Pro
        50                  55                  60

Ser Arg Pro Pro Arg Tyr Ser Ser Ser Ile Pro Glu Pro Phe Gly
65                  70                  75                  80

Ser Arg Gly Ser Pro Arg Lys Ala Ala Thr Asp Gly Ala Asp Thr Pro
                85                  90                  95
```

-continued

```
Phe Gly Arg Ser Glu Ser Ala Pro Thr Leu His Pro Tyr Ser Pro Leu
            100                 105                 110

Ser Pro Lys Gly Arg Pro Ser Ser Pro Arg Thr Pro Leu Tyr Leu Gln
            115                 120                 125

Pro Asp Ala Tyr Gly Ser Leu Asp Arg Ala Thr Ser Pro Arg Pro Arg
            130                 135                 140

Ala Phe Asp Gly Ala Gly Ser Ser Leu Gly Arg Ala Pro Ser Pro Arg
145                 150                 155                 160

Pro Gly Pro Gly Pro Leu Arg Gln Gln Gly Pro Pro Thr Pro Phe Asp
                    165                 170                 175

Phe Leu Gly Arg Ala Gly Ser Pro Arg Gly Ser Pro Leu Ala Glu Gly
            180                 185                 190

Pro Gln Ala Phe Phe Pro Glu Arg Gly Pro Ser Pro Arg Pro Pro Ala
            195                 200                 205

Thr Ala Tyr Asp Ala Pro Ala Ser Ala Phe Gly Ser Ser Leu Ile Gly
            210                 215                 220

Ser Gly Gly Ser Ala Phe Ala Pro Pro Leu Arg Ala Gln Asp Asp Leu
225                 230                 235                 240

Thr Leu Arg Arg Arg Pro Pro Lys Ala Trp Asn Glu Ser Asp Leu Asp
                    245                 250                 255

Val Ala Tyr Glu Lys Lys Pro Ser Gln Thr Ala Ser Tyr Glu Arg Leu
            260                 265                 270

Asp Val Phe Ala Arg Pro Ala Ser Pro Ser Leu Gln Leu Leu Pro Trp
            275                 280                 285

Arg Glu Ser Ser Leu Asp Gly Leu Gly Gly Thr Gly Lys Asp Asn Leu
            290                 295                 300

Thr Ser Ala Thr Leu Pro Arg Asn Tyr Lys Val Ser Pro Leu Ala Ser
305                 310                 315                 320

Asp Arg Arg Ser Asp Ala Gly Ser Tyr Arg Arg Ser Leu Gly Ser Ala
                    325                 330                 335

Gly Pro Ser Gly Thr Leu Pro Arg Ser Trp Gln Pro Val Ser Arg Ile
            340                 345                 350

Pro Met Pro Pro Ser Ser Pro Gln Pro Arg Gly Ala Pro Arg Gln Arg
            355                 360                 365

Ser Ile Pro Ser Met Ile Phe Lys Leu Gln Asn Ala Phe Trp Glu His
            370                 375                 380

Gly Ala Ser Arg Ala Met Leu Pro Gly Ser Pro Leu Phe Thr Arg Ala
385                 390                 395                 400

Pro Pro Pro Lys Leu Gln Pro Gln Pro Gln Pro Gln Pro Gln Pro Gln
                    405                 410                 415

Ser Gln Pro Gln Pro Gln Leu Pro Pro Gln Pro Gln Thr Gln Pro Gln
            420                 425                 430

Thr Pro Thr Pro Ala Pro Gln His Pro Gln Gln Thr Trp Pro Pro Val
            435                 440                 445

Asn Glu Gly Pro Pro Lys Pro Pro Thr Glu Leu Glu Pro Glu Pro Glu
            450                 455                 460

Ile Glu Gly Leu Leu Thr Pro Val Leu Glu Ala Gly Asp Val Asp Glu
465                 470                 475                 480

Gly Pro Val Ala Arg Pro Leu Ser Pro Thr Arg Leu Gln Pro Ala Leu
                    485                 490                 495

Pro Pro Glu Ala Gln Ser Val Pro Glu Leu Glu Glu Val Ala Arg Val
            500                 505                 510
```

```
Leu Ala Glu Ile Pro Arg Pro Leu Lys Arg Arg Gly Ser Met Glu Gln
        515                 520                 525

Ala Pro Ala Val Ala Leu Pro Pro Thr His Lys Lys Gln Tyr Gln Gln
    530                 535                 540

Ile Ile Ser Arg Leu Phe His Arg His Gly Pro Gly Pro Gly Gly
545                 550                 555                 560

Pro Glu Pro Glu Leu Ser Pro Ile Thr Glu Gly Ser Glu Ala Arg Ala
                565                 570                 575

Gly Pro Pro Ala Pro Ala Pro Ala Pro Ile Pro Pro Pro Ala Pro
                580                 585                 590

Ser Gln Ser Ser Pro Pro Glu Gln Pro Gln Ser Met Glu Met Arg Ser
            595                 600                 605

Val Leu Arg Lys Ala Gly Ser Pro Arg Lys Ala Arg Arg Ala Arg Leu
    610                 615                 620

Asn Pro Leu Val Leu Leu Leu Asp Ala Ala Leu Thr Gly Glu Leu Glu
625                 630                 635                 640

Val Val Gln Gln Ala Val Lys Glu Met Asn Asp Pro Ser Gln Pro Asn
                645                 650                 655

Glu Glu Gly Ile Thr Ala Leu His Asn Ala Ile Cys Gly Ala Asn Tyr
                660                 665                 670

Ser Ile Val Asp Phe Leu Ile Thr Ala Gly Ala Asn Val Asn Ser Pro
    675                 680                 685

Asp Ser His Gly Trp Thr Pro Leu His Cys Ala Ala Ser Cys Asn Asp
    690                 695                 700

Thr Val Ile Cys Met Ala Leu Val Gln His Gly Ala Ala Ile Phe Ala
705                 710                 715                 720

Thr Thr Leu Ser Asp Gly Ala Thr Ala Phe Glu Lys Cys Asp Pro Tyr
                725                 730                 735

Arg Glu Gly Tyr Ala Asp Cys Ala Thr Ser Leu Ala Asp Val Glu Gln
                740                 745                 750

Ser Met Gly Leu Met Asn Ser Gly Ala Val Tyr Ala Leu Trp Asp Tyr
    755                 760                 765

Ser Ala Glu Phe Gly Asp Glu Leu Ser Phe Arg Glu Gly Glu Ser Val
    770                 775                 780

Thr Val Leu Arg Arg Asp Gly Pro Glu Glu Thr Asp Trp Trp Ala
785                 790                 795                 800

Ala Leu His Gly Gln Glu Gly Tyr Val Pro Arg Asn Tyr Phe Gly Leu
                805                 810                 815

Phe Pro Arg Val Lys Pro Gln Arg Ser Lys Val
                820                 825
```

<210> SEQ ID NO 4
<211> LENGTH: 3156
<212> TYPE: DNA
<213> ORGANISM: Homo sapiens

<400> SEQUENCE: 4

```
gctggaggaa gccccccaggt gccaggatct gcccggatcc gcgcccgctc cggccggcac    60
catggacagc gaggcattcc agagcgcgcg ggactttctg acatgaact tccagtcgct    120 ggccatgaaa cacatggatc tgaagcagat ggagctggac acggcggcgg ccaaggtgga   180
tgaactgacc aagcagctgg agtcgctgtg gtcagactct cccgcgcctc ctggcccgca   240
ggccggaccc ccttctaggc cgccccggta cagctccagc tcgatccctg agcccttcgg   300
cagccgaggg tcccccccgga aggcggccac cgacggcgca gacacccccgt tcggacgatc   360
```

-continued

```
agagagtgcc ccaaccctac acccctacag cccgctgtcc cccaagggac ggccgtcktc    420
gccgcgcacc ccgctctacc tgcagccgga cgcctacggc agcctggacc gcgcgacctc    480
gccccgrccc cgcgccttcg atggcgcagg cagctccctc ggccgkgcgc cctccccgmg    540
gcccgggcca ggcccgctcc gccagcaggg tcccccacg cctttcgact tcctgggccg     600
cgcaggctcc ccccgcggca gcccctggcc ggaggggccc caggccttct tccccgagcg    660
tgggccgtca ccgcgccccc ctgccacagc ctacgacgcg ccagcgtccg ccttcgggag    720
ctccctgata ggctccggcg gcagcgcatt cgccccgcct ctgcgcgcgc aagacgacct    780
gacgctgcgc cggcggcctc cgaaagcctg gaacgagtct gacctggacg tggcgtacga    840
gaagaagcct tcgcagacag cgagctatga acgcctggac gtcttcgcaa ggcctgcctc    900
gccgagcctg cagctgttgc cttggaggga gagcagcctg gatggactgg ggggcaccgg    960
caaggacaac ctcactagcg ccaccctgcc gcgcaattac aaggtctctc ctctggccag   1020
cgaccggcgt tcagacgcgg gcagctaccg gcgctcgctg ggctccgcgg ggccgtcggg   1080
cactttgcct cgcagctggc agcccgtcag ccgcatcccc atgccccccct ccagccccca   1140
gccccgcggg gccccgcgcc agcgttccat ccccagcatg atcttcaagc tgcagaacgc   1200
cttctgggag cacggggcca gccgcgccat gctccctggg tccccctct tcacccgagc    1260
accccgcct aagctgcagc cccaaccaca accacagccc cagccacaat cacaaccaca    1320
gccccagctg cccccacagc cccagaccca accccaaacc cctacccccag ccccccagca   1380
tccccaacag acatggcccc ctgtgaacga aggacccccc aaacccccca ccgagctgga   1440
gcctgagccg gagatagagg ggctgctgac accagtgctg gaggctggcg atgtggatga   1500
aggccctgta gcaaggcctc tcagccccac gaggctgcag ccagcactgc caccggaggc   1560
acagtcggtg cccgagctgg aggaggtggc acgggtgttg gcggaaattc cccggcccct   1620
caaacgcagg ggctccatgg agcaggcccc tgctgtggcc ctgcccccta cccacaagaa   1680
acagtaccag cagatcatca gccgcctctt ccatcgtcat ggggggccag ggcccggggg   1740
gccggagcca gagctgtccc ccatcactga gggatctgag gccagggcag ggcccccttgc   1800
tcctgcccca ccagctccca ttccacccccc ggcccgtcc cagagcagcc caccagagca   1860
gccgcagagc atggagatgc gctctgtgct cggaaggcg ggctccccgc gcaaggcccg    1920
ccgcgcgcgc ctcaacccctc tggtgctcct cctggacgcg gcgctgaccg gggagctgga   1980
ggtggtgcag caggcggtga aggagatgaa cgacccgagc cagcccaacg aggagggcat   2040
cactgccttg cacaacgcca tctgcggcgc caactactct atcgtggatt tcctcatcac   2100
cgcgggtgcc aatgtcaact cccccgacag ccacggctgg acaccccttgc actgcgcggc   2160
gtcgtgcaac gacacagtca tctgcatggc gctggtgcag cacggcgctg caatcttcgc   2220
caccacgctc agcgacggcg ccaccgcctt cgagaagtgc gacccttacc gcagggtta   2280
tgctgactgc gccacctccc tggcagacgt cgagcagagt atgggctga tgaacagcgg   2340
ggcagtgtac gctctctggg actacagcgc cgagttcggg gacgagctgt ccttccgcga   2400
gggcgagtcg gtcaccgtgc tgcggaggga cgggccggag gagaccgact ggtggtgggc   2460
cgcgctgcac ggccaggagg gctacgtgcc gcggaactac ttcgggctgt tccccagggt   2520
gaagcctcaa aggagtaaag tctagcagga tagaaggagg tttctgaggc tgacagaaac   2580
aagcattcct gccttccctc cagacctctc cctctgtttt ttgctgcctt tatctgcacc   2640
cctcaccctg ctggtggtgg tccttgccac cggttctctg ttctcctgga agtccaggga   2700
```

```
                                       -continued
agaaggaggg ccccagcctt aaatttagta atctgcctta gccttgggag gtctgggaag    2760
ggctggaaat cactggggac aggaaaccac ttccttttgc caaatcagat cccgtccaaa    2820
gtgcctccca tgcctaccac catcatcaca tcccccagca agccagccac ctgcccagcc    2880
gggcctggga tgggccacca caccactgga tattcctggg agtcactgct gacaccatct    2940
ctcccagcag tcttggggtc tgggtgggaa acattggtct ctaccaggat ccctgcccca    3000
cctctcccca attaagtgcc ttcacacagc actggtttaa tgtttataaa caaaatagag    3060
aaactggttt aatgtttata aacaaaatag agaaactttc gcttataaat aaaagtagtt    3120
tgcacagaaa tgaaaaaaaa aaaaaaaaaa aaaaaa                              3156
```